US007056519B2

(12) United States Patent
Boudet et al.

(10) Patent No.: US 7,056,519 B2

(45) Date of Patent: Jun. 6, 2006

(54) METHODS FOR INDUCING HIV-NEUTRALIZING ANTIBODIES

(75) Inventors: Florence Boudet, Lyons (FR); Raphaëlle El Habib, Chaponost (FR); Tino Krell, Ecully (FR); Régis Sodoyer, Sainte Foy les Lyon (FR); Michel Chevalier, Beaurepaire (FR)

(73) Assignee: Aventis Pasteur S.A., Lyons (FR)

( * ) Notice: Subject to any disclaimer, the term of this patent is extended or adjusted under 35 U.S.C. 154(b) by 120 days.

(21) Appl. No.: 10/438,691

(22) Filed: May 15, 2003

(65) Prior Publication Data

US 2004/0009188 A1 Jan. 15, 2004

Related U.S. Application Data

(60) Provisional application No. 60/388,676, filed on Jun. 13, 2002.

(30) Foreign Application Priority Data

May 17, 2002 (FR) .................................. 02 06062

(51) Int. Cl.
*A61K 39/385* (2006.01)

(52) U.S. Cl. .............................. 424/193.1; 424/188.1; 424/194.1; 424/196.11; 424/208.1; 530/330; 530/324; 530/350

(58) Field of Classification Search ................ 530/350, 530/324, 330; 424/188.1, 208.1, 193.1, 194.1, 424/196.11
See application file for complete search history.

(56) References Cited

FOREIGN PATENT DOCUMENTS

| | | | |
|---|---|---|---|
| WO | WO 00 08167 | 2/2000 | .................... 15/49 |
| WO | WO 00 40616 | 7/2000 | |
| WO | WO 01 44286 | 6/2001 | |
| WO | WO 01 70262 | 9/2001 | .................... 39/12 |

OTHER PUBLICATIONS

Ho et al. "Human immunodeficiency virus neutralizing antibodies recognize several conserved domains on the envelope glycoproteins." Journal of Virology, vol. 61, No. 6 (Jun. 1987), pp. 2024-2028.*

Earl et al. "Immunogenicity and protective efficacy of oligomeric human immunodeficiency virus type 1 gp140", Journal of virolgoy, vol. 75, No. 2 (Jan. 2001), pp. 645-653.*

Cleveland et al. "Immunogenic and antigenic dominance of a nonneutralizing epitope over a highly conserved neutralizing epitope in the gp41 envelope glycoprotein of human immunodeficiency virus type 1: its deletion leads to a strong neutralizing response", Virology, vol. 266, No. 1, (Jan. 5, 2000) pp. 66-78.*

Weng, Yongkai and Weiss, Carol D., "Mutational Analysis of Residues in the Coiled-Coil Domain of Human Immunofeficiency Virus Type 1 Transmembrane Protein gp41," Journal of Virology, Dec. 1998, pp. 9676-9682.

Cao, et al., "Effects of Amino Acid Changes in the Extracellular Domain of the Human Immunodeficiency Virus Type 1 gp41 Envelope Glycoprotein," Journal of Virology, May 1993, pp. 2747-2755.

Weng, et al., "Structure-Function Studies of the Self-Assembly Domain of the Human Immunodificiency Virus Type 1 Transmembrane Protein gp41," Journal of Virology, Jun. 2000, pp. 5368-5372.

LaCasse, et al., "Fusion-Competent Vaccines: Broad Neutralization of Primary Isolates of HIV," Research Articles, Jan. 15, 1999 vol. 383.

Weissenhorn, et al., "Atomic Structure of the Ectodomain from HIV-1 gp41," Nature, vol. 387, May 1997.

Malashkevich, et al., "Crystal Structure of the Simian Immunodeficiency Virus (SIV) gp41 core: Conserved Helical Interactions Underlie the Broad Inhibitory Activity of gp41 Peptides," Proc. Natl. Acad. Sci. USA vol. 95, pp. 9134-9139, Aug. 1998 Biochemistry.

Montefiori, David C. and Evans, Thomas G., "Toward an HIV Type 1 Vaccine that Generates Potent, Broadly Cross-Reactive Neutralizing Antibodies," Aids Research and Human Retroviruses, vol. 15, No. 8, 1999, pp. 689-698.

Shu, et al., "Helical Interactions in the HIV-1 gp41 Core Reveal Structural Basis for the Inhibitory Activity of gp41 Peptides," Biochemistry 2000, 39, 1634-1642.

Louis, et al., "Design and Properties of Nccg-gp41, a Chimeric gp41 Molecule with Nanomolar HIV Fusion Inhibitory Activity," vol. 276, No. 31, Issue of Aug. 3, pp. 29485-29489, 2001.

Wingfield, et al., "The extracellular Domain of Immunodeficiency Virus gp41 Protein: Expression in *Escherichia coli*, Purification, and Crystallization," Protein Science (1997), 6:1653-1660, Cambridge University Press.

DeRosny, et al., "Petptides Corresponding to the Heptad Repeat Motifs in the Transmemebrane Protein (gp41) of Human Immunodeficiency Virus Type 1 Elicit Antibodies of Receptor-Activated Conformations of the Envelope Glycoprotein," Journal of Virology, Sep. 2001, pp. 8859-8863.

Yang, et al., "The Crystal Structure of the SIV gp41 Ectodomain at 1.47 A Resolution," Journal of Structural Biology, 126, 131-144 (1999).

Caffrey, et al., "Three-Dimensional Solution Structure of the 44 kDa Ectodomain of SIV gp41," The EMBO Journal vol. 17, No. 16, pp. 4572-4584, 1998.

* cited by examiner

*Primary Examiner*—Jeffrey Stucker
(74) *Attorney, Agent, or Firm*—McDonnell Boehnen; Hulbert & Berghoff LLP

(57) ABSTRACT

The present invention relates to a method for inducing antibodies neutralizing HIV primary isolates in a mammal, comprising administration of a pharmaceutical composition comprising a polypeptide represented by the formula N-L-C, in which:
N represents the amino acid sequence 25–81 of gp41,
C represents the amino acid sequence 112–157 of gp41, and
L represents a flexible linking sequence comprising from 2 to 30 amino acids.

8 Claims, No Drawings

SEQUENCE LISTING

```
<160> NUMBER OF SEQ ID NOS: 8

<210> SEQ ID NO 1
<211> LENGTH: 57
<212> TYPE: PRT
<213> ORGANISM: Artificial Sequence
<220> FEATURE:
<223> OTHER INFORMATION: Description of the artificial sequence:
      N-terminal residues 25-81 of gp41 of HIV-1 LAI

<400> SEQUENCE: 1

Thr Leu Thr Val Gln Ala Arg Gln Leu Leu Ser Gly Ile Val Gln Gln
  1               5                  10                  15

Gln Asn Asn Leu Leu Arg Ala Ile Glu Ala Gln Gln His Leu Leu Gln
             20                  25                  30

Leu Thr Val Trp Gly Ile Lys Gln Leu Gln Ala Arg Ile Leu Ala Val
         35                  40                  45

Glu Arg Tyr Leu Lys Asp Gln Gln Leu
     50                  55


<210> SEQ ID NO 2
<211> LENGTH: 46
<212> TYPE: PRT
<213> ORGANISM: Artificial Sequence
<220> FEATURE:
<223> OTHER INFORMATION: Description of the artificial sequence:
      C-terminal residues 112-157 of gp41 of HIV-1 LAI

<400> SEQUENCE: 2

Trp Asn Asn Met Thr Trp Met Glu Trp Asp Arg Glu Ile Asn Asn Tyr
  1               5                  10                  15

Thr Ser Leu Ile His Ser Leu Ile Glu Glu Ser Gln Asn Gln Gln Glu
             20                  25                  30

Lys Asn Glu Gln Glu Leu Leu Glu Leu Asp Lys Trp Ala Ser
         35                  40                  45


<210> SEQ ID NO 3
```

-continued

<211> LENGTH: 103
<212> TYPE: PRT
<213> ORGANISM: Artificial Sequence
<220> FEATURE:
<223> OTHER INFORMATION: Description of the artificial sequence:
ectodomain of gp41 of HIV-1 LAI

<400> SEQUENCE: 3

```
Thr Leu Thr Val Gln Ala Arg Gln Leu Leu Ser Gly Ile Val Gln Gln
  1               5                  10                  15

Gln Asn Asn Leu Leu Arg Ala Ile Glu Ala Gln Gln His Leu Leu Gln
             20                  25                  30

Leu Thr Val Trp Gly Ile Lys Gln Leu Gln Ala Arg Ile Leu Ala Val
         35                  40                  45

Glu Arg Tyr Leu Lys Asp Gln Gln Leu Trp Asn Asn Met Thr Trp Met
     50                  55                  60

Glu Trp Asp Arg Glu Ile Asn Asn Tyr Thr Ser Leu Ile His Ser Leu
 65                  70                  75                  80

Ile Glu Glu Ser Gln Asn Gln Gln Glu Lys Asn Glu Gln Glu Leu Leu
                 85                  90                  95

Glu Leu Asp Lys Trp Ala Ser
            100
```

<210> SEQ ID NO 4
<211> LENGTH: 113
<212> TYPE: PRT
<213> ORGANISM: Artificial Sequence
<220> FEATURE:
<223> OTHER INFORMATION: Description of the artificial sequence:
ectodomain of gp41 with ERDRD epitope tag at C-terminus

<400> SEQUENCE: 4

```
Thr Leu Thr Val Gln Ala Arg Gln Leu Leu Ser Gly Ile Val Gln Gln
  1               5                  10                  15

Gln Asn Asn Leu Leu Arg Ala Ile Glu Ala Gln Gln His Leu Leu Gln
             20                  25                  30

Leu Thr Val Trp Gly Ile Lys Gln Leu Gln Ala Arg Ile Leu Ala Val
         35                  40                  45

Glu Arg Tyr Leu Lys Asp Gln Gln Leu Trp Asn Asn Met Thr Trp Met
     50                  55                  60

Glu Trp Asp Arg Glu Ile Asn Asn Tyr Thr Ser Leu Ile His Ser Leu
 65                  70                  75                  80

Ile Glu Glu Ser Gln Asn Gln Gln Glu Lys Asn Glu Gln Glu Leu Leu
                 85                  90                  95

Glu Leu Asp Lys Trp Ala Ser Gly Gly Gly Gly Ser His His His His
            100                 105                 110

His
```

<210> SEQ ID NO 5
<211> LENGTH: 23
<212> TYPE: DNA
<213> ORGANISM: Artificial Sequence
<220> FEATURE:
<223> OTHER INFORMATION: Description of the artificial sequence: 5'
primer

<400> SEQUENCE: 5

```
tcatgacgct gacggtacag gcc                                            23
```

<210> SEQ ID NO 6

-continued

<211> LENGTH: 63
<212> TYPE: DNA
<213> ORGANISM: Artificial Sequence
<220> FEATURE:
<223> OTHER INFORMATION: Description of the artificial sequence: 3' primer

<400> SEQUENCE: 6
ccgctcgagc taatggtgat ggtgatggtg tgaccctccc cctccacttg cccatttatc 60
taa 63

<210> SEQ ID NO 7
<211> LENGTH: 5312
<212> TYPE: DNA
<213> ORGANISM: Artificial Sequence
<220> FEATURE:
<223> OTHER INFORMATION: Description of the artificial sequence: plasmid Pet-cer

<400> SEQUENCE: 7
tggcgaatgc cttaattaag gcggggcaca actcaatttg cgggtactga ttaccgcagc 60
aaagacctta ccccgaaaaa atccaggctg ctggctgaca cgatttctgc ggtttatctc 120
gatggctacg agggcagaca gtaagtggat ttaccataat cccttaattg tacgcaccgc 180
taaaacgcgt tcagcgcgat cacggcagca gacaggtaaa aatggcaaca aaccacccga 240
aaaactgccg cgatcgcgcc tgataaattt taaccgtatg aatacctatg caaccagagg 300
gtacaggcca cattaccccc acttaatcca ctgaagctgc catttttcat ggtttcacca 360
tcccagcgaa gggccatcca gcgtgcgttc ctgtatttcc gactggcgcg ccattcaggt 420
ggcacttttc ggggaaatgt gcgcggaacc cctatttgtt tatttttcta aatacattca 480
aatatgtatc cgctcatgaa ttaattctta gaaaaactca tcgagcatca aatgaaactg 540
caatttattc atatcaggat tatcaatacc atatttttga aaaagccgtt tctgtaatga 600
aggagaaaac tcaccgaggc agttccatag gatggcaaga tcctggtatc ggtctgcgat 660
tccgactcgt ccaacatcaa tacaacctat taatttcccc tcgtcaaaaa taaggttatc 720
aagtgagaaa tcaccatgag tgacgactga atccggtgag aatggcaaaa gtttatgcat 780
ttctttccag acttgttcaa caggccagcc attacgctcg tcatcaaaat cactcgcatc 840
aaccaaaccg ttattcattc gtgattgcgc ctgagcgaga cgaaatacgc gatcgctgtt 900
aaaaggacaa ttacaaacag gaatcgaatg caaccggcgc aggaacactg ccagcgcatc 960
aacaatattt tcacctgaat caggatattc ttctaatacc tggaatgctg ttttcccggg 1020
gatcgcagtg gtgagtaacc atgcatcatc aggagtacgg ataaaatgct tgatggtcgg 1080
aagaggcata aattccgtca gccagtttag tctgaccatc tcatctgtaa catcattggc 1140
aacgctacct ttgccatgtt tcagaaacaa ctctggcgca tcgggcttcc catacaatcg 1200
atagattgtc gcacctgatt gcccgacatt atcgcgagcc catttatacc catataaatc 1260
agcatccatg ttggaattta atcgcggcct agagcaagac gtttcccgtt gaatatggct 1320
cataacaccc cttgtattac tgtttatgta agcagacagt tttattgttc atgaccaaaa 1380
tcccttaacg tgagttttcg ttccactgag cgtcagaccc cgtagaaaag atcaaaggat 1440
cttcttgaga tcctttttt ctgcgcgtaa tctgctgctt gcaaacaaaa aaaccaccgc 1500
taccagcggt ggtttgtttg ccggatcaag agctaccaac tctttttccg aaggtaactg 1560
gcttcagcag agcgcagata ccaaatactg tccttctagt gtagccgtag ttaggccacc 1620
acttcaagaa ctctgtagca ccgcctacat acctcgctct gctaatcctg ttaccagtgg 1680

-continued

```
ctgctgccag tggcgataag tcgtgtctta ccgggttgga ctcaagacga tagttaccgg   1740
ataaggcgca gcggtcgggc tgaacggggg gttcgtgcac acagcccagc ttggagcgaa   1800
cgacctacac cgaactgaga tacctacagc gtgagctatg agaaagcgcc acgcttcccg   1860
aagggagaaa ggcggacagg tatccggtaa gcggcagggt cggaacagga gagcgcacga   1920
gggagcttcc agggggaaac gcctggtatc tttatagtcc tgtcgggttt cgccacctct   1980
gacttgagcg tcgatttttg tgatgctcgt caggggggcg gagcctatgg aaaaacgcca   2040
gcaacgcggc ctttttacgg ttcctggcct tttgctggcc ttttgctcac atgttctttc   2100
ctgcgttatc ccctgattct gtgggtaacc gtattaccgc ctttgagtga gctgataccg   2160
ctcgccgcag ccgaacgacc gagcgcagcg agtcagtgag cgaggaagcg gaagagcgcc   2220
tgatgcggta ttttctcctt acgcatctgt gcggtatttc acaccgcaat ggtgcactct   2280
cagtacaatc tgctctgatg ccgcatagtt aagccagtat acactccgct atcgctacgt   2340
gactgggtca tggctgcgcc ccgacacccg ccaacacccg ctgacgcgcc ctgacgggct   2400
tgtctgctcc cggcatccgc ttacagacaa gctgtgaccg tctccgggag ctgcatgtgt   2460
cagaggtttt caccgtcatc accgaaacgc gcgaggcagc tgcggtaaag ctcatcagcg   2520
tggtcgtgaa gcgattcaca gatgtctgcc tgttcatccg cgtccagctc gttgagtttc   2580
tccagaagcg ttaatgtctg gcttctgata aagcgggcca tgttaagggc ggtttttttcc  2640
tgtttggtca ctgatgcctc cgtgtaaggg ggatttctgt tcatgggggt aatgataccg   2700
atgaaacgag agaggatgct cacgatacgg gttactgatg atgaacatgc ccggttactg   2760
gaacgttgtg agggtaaaca actggcggta tggatgcggc gggaccagag aaaaatcact   2820
cagggtcaat gccagcgctt cgttaataca gatgtaggtg ttccacaggg tagccagcag   2880
catcctgcga tgcagatccg gaacataatg gtgcagggcg ctgacttccg cgtttccaga   2940
ctttacgaaa cacggaaacc gaagaccatt catgttgttg ctcaggtcgc agacgttttg   3000
cagcagcagt cgcttcacgt tcgctcgcgt atcggtgatt cattctgcta accagtaagg   3060
caaccccgcc agcctagccg ggtcctcaac gacaggagca cgatcatgcg cacccgtggg   3120
gccgccatgc cggcgataat ggcctgcttc tcgccgaaac gtttggtggc gggaccagtg   3180
acgaaggctt gagcgagggc gtgcaagatt ccgaataccg caagcgacag gccgatcatc   3240
gtcgcgctcc agcgaaagcg gtcctcgccg aaaatgaccc agagcgctgc cggcacctgt   3300
cctacgagtt gcatgataaa gaagacagtc ataagtgcgg cgacgatagt catgccccgc   3360
gcccaccgga aggagctgac tgggttgaag gctctcaagg gcatcggtcg agatcccggt   3420
gcctaatgag tgagctaact tacattaatt gcgttgcgct cactgcccgc tttccagtcg   3480
ggaaacctgt cgtgccagct gcattaatga atcggccaac gcgcggggag aggcggtttg   3540
cgtattgggc gccagggtgg tttttctttt caccagtgag acgggcaaca gctgattgcc   3600
cttcaccgcc tggccctgag agagttgcag caagcggtcc acgctggttt gccccagcag   3660
gcgaaaatcc tgtttgatgg tggttaacgg cgggatataa catgagctgt cttcggtatc   3720
gtcgtatccc actaccgaga tatccgcacc aacgcgcagc ccggactcgg taatggcgcg   3780
cattgcgccc agcgccatct gatcgttggc aaccagcatc gcagtgggaa cgatgccctc   3840
attcagcatt tgcatggttt gttgaaaacc ggacatggca ctccagtcgc cttcccgttc   3900
cgctatcggc tgaatttgat tgcgagtgag atatttatgc cagccagcca gacgcagacg   3960
cgccgagaca gaacttaatg ggcccgctaa cagcgcgatt tgctggtgac ccaatgcgac   4020
```

-continued

```
cagatgctcc acgcccagtc gcgtaccgtc ttcatgggag aaaataatac tgttgatggg   4080

tgtctggtca gagacatcaa gaaataacgc cggaacatta gtgcaggcag cttccacagc   4140

aatggcatcc tggtcatcca gcggatagtt aatgatcagc ccactgacgc gttgcgcgag   4200

aagattgtgc accgccgctt tacaggcttc gacgccgctt cgttctacca tcgacaccac   4260

cacgctggca cccagttgat cggcgcgaga tttaatcgcc gcgacaattt gcgacggcgc   4320

gtgcagggcc agactggagg tggcaacgcc aatcagcaac gactgtttgc ccgccagttg   4380

ttgtgccacg cggttgggaa tgtaattcag ctccgccatc gccgcttcca ctttttcccg   4440

cgttttcgca gaaacgtggc tggcctggtt caccacgcgg gaaacggtct gataagagac   4500

accggcatac tctgcgacat cgtataacgt tactggtttc acattcacca ccctgaattg   4560

actctcttcc gggcgctatc atgccatacc gcgaaaggtt ttgcgccatt cgatggtgtc   4620

cgggatctcg acgctctccc ttatgcgact cctgcattag gaagcagccc agtagtaggt   4680

tgaggccgtt gagcaccgcc gccgcaagga atggtgcatg caaggagatg gcgcccaaca   4740

gtcccccggc cacggggcct gccaccatac ccacgccgaa acaagcgctc atgagcccga   4800

agtggcgagc ccgatcttcc ccatcggtga tgtcggcgat ataggcgcca gcaaccgcac   4860

ctgtggcgcc ggtgatgccg gccacgatgc gtccggcgta gaggatcgag atctcgatcc   4920

cgcgaaatta atacgactca ctatagggga attgtgagcg gataacaatt cccctctaga   4980

aataattttg tttaacttta agaaggagat ataccatggg cagcagccat catcatcatc   5040

atcacagcag cggcctggtg ccgcgcggca gccatatggc tagcatgact ggtggacagc   5100

aaatgggtcg gatccgaatt cgagctccgt cgacaagctt gcggccgcac tcgagcacca   5160

ccaccaccac cactgagatc cggctgctaa caaagcccga aaggaagctg agttggctgc   5220

tgccaccgct gagcaataac tagcataacc ccttggggcc tctaaacggg tcttgagggg   5280

tttttgctg aaaggaggaa ctatatccgg at                                  5312


<210> SEQ ID NO 8
<211> LENGTH: 200
<212> TYPE: PRT
<213> ORGANISM: Artificial Sequence
<220> FEATURE:
<223> OTHER INFORMATION: Description of the artificial sequence:
      fragment of gp41

<400> SEQUENCE: 8

Ala Val Gly Ile Gly Ala Leu Phe Leu Gly Phe Leu Gly Ala Ala Gly
  1               5                  10                  15

Ser Thr Met Gly Ala Ala Ser Met Thr Leu Thr Val Gln Ala Arg Gln
             20                  25                  30

Leu Leu Ser Gly Ile Val Gln Gln Gln Asn Asn Leu Leu Arg Ala Ile
         35                  40                  45

Glu Ala Gln Gln His Leu Leu Gln Leu Thr Val Trp Gly Ile Lys Gln
     50                  55                  60

Leu Gln Ala Arg Ile Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
        115                 120                 125
```

-continued

```
Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Asn Arg Val Arg
                165                 170                 175

Gln Gly Tyr Ser Pro Leu Ser Phe Gln Thr His Leu Pro Thr Pro Arg
            180                 185                 190

Gly Pro Asp Arg Pro Glu Gly Ile
        195                 200
```

METHODS FOR INDUCING HIV-NEUTRALIZING ANTIBODIES

The present invention relates to a polypeptide antigen which derives from the gp41 protein, and also to the use thereof for immunization against HIV-related infection.

These studies were cofinanced by the ANRS [French National Association for AIDS Research].

The integrality of the various articles and documents cited here is incorporated here by reference.

The development of a method of immunization against HIV is, today, one of the priorities of scientific research.

The major obstacles represented by the great genetic variability of the virus and the low exposure to the immune system of conserved neutralizing viral epitopes considerably hinder the development of a vaccine capable of neutralizing HIV primary isolates.

The HIV envelope glycoprotein, which is required to confer on the virus its infectious nature, represents the target for neutralizing antibodies. These characteristics have made this target a subject of intense investigation.

The use, for immunization purposes, of polypeptides which derive from the gp41 protein has been described in WO 00/40616. According to that application, N-helices may be used alone or in combination with C-helices, to induce neutralizing antibodies.

The Applicant here proposes a novel polypeptide antigen which can be used for therapeutic and prophylactic immunization against HIV-related infection. The Applicant has, in fact, revealed a polypeptide which derives from the ectodomain of the gp41 protein and which is capable of inducing antibodies which neutralize HIV primary isolates.

The present invention therefore relates to a polypeptide represented by the formula:

N-L-C in which:

N represents the amino acid sequence 25–81 of gp41,

C represents the amino acid sequence 112–157 of gp41, and

L represents a flexible linking sequence comprising from 2 to 30 amino acids.

According to a particular embodiment, N represents SEQ ID No.1 and C represents SEQ ID No.2.

According to a preferred embodiment, the polypeptide consists of the sequence SEQ ID No.3.

According to another embodiment, the polypeptide as defined above also comprises a sequence containing the epitope ERDRD (SEQ ID NO: 9).

According to a particular embodiment, the polypeptide as defined above comprises an additional sequence of formula (G)a-S-(H)b in which G represents a glycine residue, H represents a histidine residue, a is greater than or equal to 4 and b is greater than or equal to 6, said sequence being linked, via an amide bond, to the $NH_2$- or COOH-terminal end of the polypeptide.

According to a particularly preferred embodiment, the polypeptide according to the present invention consists of the sequence SEQ ID No.4.

A subject of the present invention is also a conjugate comprising a polypeptide as defined above, conjugated to a carrier protein or peptide.

The present invention also relates to a DNA sequence encoding a polypeptide or a conjugate as defined above.

A subject of the present invention is also an expression vector comprising said DNA sequence.

According to a preferred embodiment, the DNA encodes a polypeptide as defined above which also comprises a sequence containing the epitope ERDRD (SEQ ID NO: 9).

A subject of the present invention is also a host cell containing the vector as defined above.

According to another aspect, the present invention relates to a method for preparing a polypeptide as defined above, comprising expression of said polypeptide using a host cell as defined above.

According to another aspect, the present invention relates to a pharmaceutical composition comprising at least one polypeptide, at least one conjugate or at least one expression vector as defined above, a pharmaceutically acceptable excipient and, optionally, an adjuvant.

According to a particular embodiment, the pharmaceutical composition comprises a polypeptide of sequence SEQ ID No.4 and an adjuvant selected from the group consisting of DC-Chol and aluminum gel.

A subject of the present invention is also the polypeptide as defined above, for its use as a medicinal product, in particular for inducing specific neutralizing antibodies in a mammal.

The present invention also relates to a method for inducing specific neutralizing antibodies in a mammal, comprising administration of a pharmaceutical composition as defined above and induction of said antibodies.

According to a preferred embodiment, the administration is carried out orally or intramuscularly.

The invention is described in greater detail in the following description.

The Applicant has demonstrated, surprisingly, that the polypeptide according to the invention induces specific IgG antibodies which neutralize HIV primary isolates. The induction of antibodies which neutralize primary isolates can be determined using the neutralization test as described in the article by C. Moog et al. (AIDS Research and human retroviruses, Vol. 13(1), 13–27, 1997), to which reference may be made for a complete description of the latter. In the context of the present invention, it is estimated that neutralizing antibodies have been induced by the antigen tested according to the technique of C. Moog when the serum diluted at least to ¼, in the presence of HIV, leads to a 10-fold decrease in the viral titer in comparison to HIV alone, the viral titer being evaluated by the amount of p24 produced in the culture supernatant.

The induction of antibodies which neutralize primary isolates may also be determined using the neutralization test of D. Montefiori as described in J. Infect. Dis. 1996, 173:60–67. In this test, the neutralizing titer is expressed by the percentage decrease in p24 antigen produced in the culture supernatants when the virus is incubated in the presence of serum diluted to 1/4, by comparison with the virus in the absence of serum. In the context of the present invention, it is considered that neutralizing antibodies have been induced when the decrease in the level of p24 produced reaches at least 80% with a serum diluted to ¼.

In the context of the present invention, it is considered that the antibodies induced by the polypeptide according to the invention are neutralizing antibodies if neutralizing activity is detected for a given isolate in at least one of the two tests above.

The induction of antibodies which neutralize the HIV-1 MN laboratory strain can be estimated using the MT-2 cell line according to the method of D. Montefiori, described in: D C Montefiori et al., J. Clin. Microbiol. 1988, 26: 231–5). In this method, the neutralizing titer is expressed as the inverse of the dilution of the serum (in arithmetic value)

which protects at least 50% of cells against the cytopathogenic effect of the HIV virus.

The N and C sequences which constitute the polypeptide according to the present invention may be derived from any gp41 protein of HIV, including the HIV1 and HIV2 strains, including laboratory strains and primary isolates. Preferably, the constituent sequences are derived from an HIV1 strain, and in particular from an HIV1 LAI strain.

The amino acids are numbered with reference to the sequence of the gp41 fragment SEQ ID No.8, in which the first amino acid A carries the number 1.

According to a preferred embodiment, N represents SEQ ID No.1 and C represents SEQ ID No.2.

The nucleotide and peptide sequences of a large number of gp41proteins are known and available, for example, as provided in public databases maintained by the Los Alamos National Laboratory (Los Alamos, N. Mex). It is clear that any sequence into which one or more conservative mutations which do not substantially modify immunogenicity have been introduced is also included in the context of the present invention.

The N and C sequences are linked to one another via a linking peptide sequence L comprising from 2 to 30 amino acids. This linking sequence L is a loop which allows the N and C sequences to pair with one another according to an anti-parallel orientation. The polypeptide according to the present invention is a trimer consisting of 3 N-L-C monomers forming a bundle in which the N-helices are paired with one another and the C-helices are paired with the N-helices according to an anti-parallel orientation.

The L sequences suitable in the context of the present invention may be selected using a secondary structure prediction program GOR (Gamier, Osguthorpe and Robson (1078), J. Mol. Biol., 120, 97–120on the N-L-C sequence, specifying, in the "helix" and "extended" windows, the unknown notion. The percentage of helix in the prediction of the secondary structure of L should be less than 10. The L sequences are advantageously weakly hydrophobic, preferably hydrophilic in order to facilitate purification of the corresponding polypeptide. The hydrophilic nature may be obtained by using an amino acid which is hydrophilic in nature, such as serine, which may be combined with glycines. According to a preferred embodiment, the polypeptide according to the invention has the sequence SEQ ID No.3. This sequence may advantageously be modified in order to decrease its hydrophobic nature, for example by introducing at least one of the following mutations: W85D; L91K; I92K and W103D, and preferably by introducing at least any two mutations selected from the group of the 4 mutations proposed above, or even all of said mutations.

According to a particular embodiment, the polypeptide of formula N-L-C as defined above also comprises a sequence containing the Kennedy epitope ERDRD (SEQ ID NO: 9). The ERDRD (SEQ ID NO: 9) sequence may be linked at the N- or C-terminal of the polypeptide, directly or preferably via a flexible linkage. Such a flexible linkage typically comprises about ten or so amino acids, preferably hydrophilic in nature. Sequences comprising glycines and serines, such as GGR, are, for example, perfectly suitable. The epitope ERDRD (SEQ ID NO: 9) may also be inserted into the L sequence of the polypeptide. In such a scenario, the epitope will preferentially be bordered by linking sequences which provide the junction with the N and C sequences. The nature of these sequences can be easily determined using the GOR secondary structure prediction program mentioned above, the objective being for the linking sequence L to allow anti-parallel pairing of the N- and C-helices.

In the context of the present invention, the expression "a sequence comprising the epitope ERDRD (SEQ ID NO: 9)" is therefore intended to mean a sequence consisting of the epitope ERDRD (SEQ ID NO: 9), optionally of a flexible linkage and optionally of some additional amino acids which would result from the method of constructing the plasmids expressing the polypeptide, due to the use of restriction sites. This is the case, for example, of the amino acids RSGGGGS (SEQ ID NO: 10) present at the C-terminal of the constructs tested in example 4.

The polypeptide according to the invention may be obtained by any conventional technique of chemical synthesis or of genetic engineering.

When the polypeptide is produced by chemical synthesis, the polypeptide according to the invention may be synthesized in the form of a single sequence, or in the form of several sequences which are then linked to one another. The chemical synthesis may be carried out in solid phase or in solution, these two synthesis techniques being well known to those skilled in the art. These techniques are in particular described by Atherton and Shepard in "Solid phase peptide synthesis" (IRL press Oxford, 1989) and by Houbenweyl in "Methoden der organischen Chemie" [Methods in Organic Chemistry] published by E.Wunsch Vol. 15-I and II, Stuttgart, 1974, and also in the following articles, which are entirely incorporated herein by way of reference: P E Dawson et al. (Science 1994; 266(5186):776–9); G G Kochendoerfer et al. (1999; 3(6):665–71); et P E Dawson et al., Annu. Rev. Biochem. 2000; 69:923–60.

The polypeptide according to the invention may also be produced using genetic engineering techniques well known to those skilled in the art. When the polypeptide according to the invention is produced by genetic engineering, it comprises, at the $NH_2$-terminal end, an additional methionine residue corresponding to the translation of the first initiation codon. These techniques are described in detail in Molecular Cloning: a molecular manual, by Maniatis et al., Cold Spring Harbor, 1989. Conventionally, the PCR technique is used to produce the DNA sequence encoding the polypeptide according to the invention in a form which can be inserted into an expression vector. The DNA sequence thus obtained is then inserted into an expression vector. The expression vector containing the sequence of interest is then used to transform a host cell which allows expression of the sequence of interest. The polypeptide produced is then isolated from the culture medium using conventional chromatography techniques well known to those skilled in the art. High performance liquid chromatography (HPLC) is preferably used in the purification. Typically, the cells are collected at the end of culturing, by centrifugation, and are taken up in a neutral buffer, in order to be ruptured by any suitable means. The cell lysate is then centrifuged at approximately 10 000 g in order to separate the soluble material from the insoluble material. SDS-PAGE analysis of the supernatant and of the pellet from centrifugation will reveal whether the polypeptide is soluble or not. If the polypeptide is insoluble, solubilization is obtained using a buffer containing urea, guanidine or other solubilizing agents. Centrifugation at this step makes it possible to remove debris and other insoluble products which would hamper the chromatography. The following step consists in loading the solubilized molecule onto an affinity column, which may be of the metal chelate type if a polyhistidine tail is integrated onto the polypeptide of interest. The system which enables the affinity purification may be varied in nature, such as immunoaffinity, affinity on cibachron blue, etc. At this stage, the protein exhibits a degree of purity close to or greater than 80%, as may be determined by SDS PAGE electrophoresis followed by coomassie blue staining. An additional chromatography step may be added in order to finish the polypeptide; by way of example, mention may be made of gel filtration and reverse-phase chromatography.

The polypeptide according to the invention may thus be obtained in purified form, i.e. in a form exhibiting a degree of purity of at least 80%. The degree of purity is defined relative to the other proteins present in the mixture which are considered to be contaminants. This degree is evaluated by colorimetry of an SDS-PAGE using coomassie blue. Densitometric measurement of the bands makes it possible to quantify the degree of purity. The degree of purity may also be measured by reverse-phase HPLC, by measuring the area of the various peaks.

In the context of the present invention, any expression vector conventionally used for the expression of a recombinant protein may be used to synthesize the polypeptide. This term therefore encompasses both "live" expression vectors, such as viruses and bacteria, and expression vectors of the plasmid type.

Use is preferably made of vectors in which the DNA sequence of the polypeptide according to the invention is under the control of the strong promoter, which may or may not be inducicble. By way of example of a promoter which may be used, mention may be made of the T7 RNA polymerase promoter.

The expression vectors preferably include at least one selectable marker. Such markers include, for example, the dihydrofolate reductase gene or the neomycin resistance gene for culturing eukaryotic cells, and the kanamycin, tetracycline or ampicillin resistance genes for culturing in *E. coli* and other bacteria.

By way of example of an expression vector which may be used in the context of the present invention, mention may be made of the plasmid pET28 (Novagen) or pBAD (Invitrogen), for example; viral vectors, such as: baculoviruses, poxviruses, in particular the poxviruses described in patents U.S. Pat No. 5,942,235, U.S. Pat. No. 5,756,103 and U.S. Pat. No. 5,990,091, which are entirely incorporated herein by way of reference, and recombinant vaccinia viruses, in particular the recombinant viruses described in patents EP 83286, U.S. Pat. No. 5,494,807 and U.S. Pat. No. 5,762,938, into which the DNA sequence encoding a polypeptide according to the invention is cloned.

In order to promote the expression and purification of the polypeptide, the latter may be expressed in a modified form, such as a fusion protein, and may include not only secretion signals, but also additional heterologous functional regions. For example, a region of additional amino acids, particularly charged amino acids, may be added at the N-terminal of the polypeptide in order to improve stability and persistence in the host cell. Advantageously, the polypeptide according to the present invention is produced in the form of a fusion peptide comprising an additional sequence of formula (G)a-S-(H)b in which G represents a glycine residue, H represents a histidine residue, and preferably a is greater than or equal to 4 and b is greater than or equal to 6, linked, via an amide bond, to the $NH_2$- or COOH-terminal end of the polypeptide. This sequence allows rapid purification of the polypeptide according to the invention by immunoaffinity.

Any host cell conventionally used in combination with the expression vectors described above may be used for expression of the polypeptide.

By way of nonlimiting examples, mention may be made of the cells of *E. coli*, BL21 (lamdaDE3), HB101, Top 10, CAG 1139, Bacillus, and eukaryotic cells such as CHO or Vero.

In the context of the present invention, use will preferably be made of the following expression vector/cell system: pET(Cer)/BL21LamdaDE3, or BL21lamdaDE3(RIL).

Depending on the host cell used for expressing the polypeptide, the polypeptides of the present invention may be glycosylated or nonglycosylated. In addition, the polypeptides according to the invention may also include an additional methionine residue at the N-terminal.

A subject of the present invention is also the conjugates comprising a polypeptide according to the invention and a carrier protein or a carrier peptide.

The carrier protein (or peptide) strengthens the immunogenicity of the polypeptide according to the invention, in particular by increasing the production of specific antibodies. Said carrier protein (or peptide) preferably comprises one or more T helper epitope(s). The term "T helper epitope" is intended to mean a chain of amino acids which, in the context of one or more class II MHC molecules, activates T helper lymphocytes. According to an advantageous embodiment, the carrier protein (or peptide) used improves the water-solubility of the polypeptide according to the invention.

As carrier protein, use may be made, for example, of phage surface proteins, such as the pIII or pVIII proteins of the M13 phage, bacterial surface proteins, such as the LamB, OmpC, ompA, ompF and PhoE proteins of *E. coli*, the CotC or CotD protein of *B. subtilis*, bacterial porins, such as *Neisseria gonorrheae* porin P1, *H. influenzae* B porin P1 or P2, *N. meningitidis* B class I porin or *K. pneumoniae* porin P40, lipoproteins, such as *B. bugdorfi* OspA, *S. pneumoniae* PspA, *N. meningitidis* B TBP2, *E. coli* TraT and also *S. pneumoniae* adhesin A, and the heat shock proteins, such as Hsp65 or Hsp71 of *M. tuberculosis* or bovis, or Hin 47 of *H. influenzae* type B. Detoxified bacterial toxins, such as tetanus or diphtheria toxoid, the cholera toxin B subunit, or the B subunit of *P. aeruginosa* endotoxin A or *S. aureus* exotoxin A, are also particularly suitable in the context of the present invention.

In the context of the present invention, as a carrier peptide, use may be made, for example, of the p24E, p24N, p24H and p24M peptides described in WO 94/29339 and also the PADRE peptides as described by Del guercio et al. (Vaccine (1997); Vol. 15/4, p. 441–448).

The carrier protein (or peptide) is linked to the N- or C-terminal end of the polypeptide according to the invention using any conjugation method well known to those skilled in the art. In addition, the sequence encoding the carrier protein (or peptide) may advantageously be fused to the sequence encoding the polypeptide according to the invention, and the resulting sequence may be expressed in the form of a fusion protein using any conventional method. All the genetic engineering techniques which are useful for doing this are described in Maniatis et al. Said conjugates may be isolated using any conventional purification method well known to those skilled in the art.

A subject of the present invention is also the DNA sequences encoding the polypeptides and the conjugates according to the invention, and also the expression vectors comprising said sequences and the host cells transformed with said vectors. The DNA sequences encoding the polypeptides according to the invention can be easily produced by PCR using, as a matrix, the nucleotide sequence of a gp41 protein.

Rather than extracting and purifying the polypeptide or the conjugate expressed by the expression vector, it is often easier and sometimes more advantageous to use the expression vector itself in the vaccine according to the invention. A subject of the present invention is therefore any expression vector as defined above. In such a situation, the expression vector lacks a marker and preferably corresponds to a viral vector, in particular a poxvirus, such as ALVAC or NYVAC. Such a vector may also contain at least one other sequence encoding an HIV antigen. By way of example, mention may be made of the HIV antigen sequences which are conventionally used in the.vectors described in patents U.S. Pat. No. 5,942,235, U.S. Pat. No. 5,756,103 and U.S. Pat. No. 5,762,938.

The expression vector according to the invention preferably comprises a sequence encoding a polypeptide of formula N-L-C as defined above, also comprising a sequence comprising the epitope ERDRD (SEQ ID NO: 9) as defined above, which is linked to the N- or C-terminal end of said polypeptide. According to a particularly preferred embodiment, the expression vector comprises a sequence encoding the polypeptide of formula: AA25-AA157-GGRERDRDRSGGGGS (SEQ ID NO: 11).

Any host cell as defined above transformed with such an expression vector is also included in the context of the present invention.

A subject of the present invention is also the antibodies directed against the polypeptides and conjugates as described above. The preparation of such antibodies is carried out using conventional techniques for producing polyclonal and monoclonal antibodies, well known to those skilled in the art.

These antibodies are particularly suitable for use in a passive immunization scheme.

A subject of the present invention is also pharmaceutical compositions which can be used for the purposes of therapeutic and prophylactic immunization against HIV-related infection. The compositions according to the present invention comprise at least one polypeptide, at least one conjugate or at least one expression vector as defined above, in an amount suitable to induce a specific humoral response, a pharmaceutically acceptable excipient or diluent and, optionally, an adjuvant.

The amount of polypeptide, of conjugate or of vector in the composition according to the present invention depends on many parameters, as will be understood by those skilled in the art, such as the nature of the carrier protein, the vector used or the route of administration. A suitable amount is an amount such that a specific humoral immune response is induced after administration of said composition. The amount of polypeptide to be administered is of the order of 10 μg to 5 mg, the amount selected varying depending on the route of administration. The amount of conjugate to be administered will be deduced from the amounts indicated above, taking into account the MW of the carrier protein. The amount of expression vector to be administered is of the order of 10 to 5 000 μg in the case of a nonviral vector, and of the order of $10^{E}4$ to $10^{E}8$ TCID50 in the case of a viral vector.

The pharmaceutical compositions according to the present invention may also contain an adjuvant. Any pharmaceutically acceptable adjuvant or mixture of adjuvants conventionally used in the field of vaccines may be used for this purpose. By way of suitable adjuvants, mention may be made of aluminum salts, such as aluminum hydroxide or aluminum phosphate, and DC-Chol. Conventional auxiliary agents, such as wetting agents, fillers, emulsifiers, buffers, etc., may also be added to the composition according to the invention.

The compositions according to the present invention may be prepared using any conventional method known to those skilled in the art. Conventionally, the antigens according to the invention (i.e. polypeptide, conjugate or vector) are mixed with a pharmaceutically acceptable excipient or diluent, such as water or phosphate-buffered saline solution. The excipient or diluent will be selected as a function of the pharmaceutical form chosen, of the method and route of administration, and also of pharmaceutical practice. Suitable excipients or diluents, and also the requirements in terms of pharmaceutical formulation, are described in detail in Remington's Pharmaceutical Sciences, which represents a reference work in this field.

The compositions mentioned above may be administered by any conventional route usually used in the field of vaccines, such as the parenteral (intramuscular, subcutaneous, etc.) route. In the context of the present invention, intramuscular administration will preferably be used for the injectable compositions. Such an administration may advantageously take place in the thigh or arm muscles. The compositions according to the present invention may also advantageously be administered orally.

In fact, the Applicant has demonstrated that the polypeptide according to the invention is very stable in strongly acid medium (pH < or = to 3). This property makes the polypeptide according to the invention an immunization antigen of choice for oral administration. In this case, it is possible to administer the polypeptide in the form of a solution having a pH < or = to 3 which may or may not contain an adjuvant. In the case of the polypeptides comprising an L sequence which is weakly hydrophobic in nature or hydrophilic in nature, a higher pH may be used. The Applicant has, in fact, shown that stability of the forms comprising loops which are more hydrophilic is obtained over a wider pH range. The polypeptides comprising such loops may therefore advantageously be used for parenteral administration. Administration via the nasal, vaginal or rectal mucosa may also be recommended in the context of the present invention. The administration may also be carried out by giving a single dose or repeated doses, for example on D0 and at 1 month, 3 months, 6 months and 12 months. Injections on D0 and at 1 month and 3 months, with a booster, the periodicity of which may be easily determined by the treating physician, will preferably be used.

The pharmaceutical composition according to the present invention may advantageously be administered according to a dosage scheme comprising the co-administration of an expression vector according to the invention and of a polypeptide according to the invention, or according to a "prime-boost" scheme in which the vector according to the invention is administered first and the polypeptide is administered as a booster injection. In these two dosage schemes, the expression vector according to the invention may be replaced with any expression vector expressing one or more HIV antigens or epitopes which are different from the polypeptide according to the invention, and in particular with a poxvirus, preferably ALVAC or NYVAC. By way of example of ALVAC and NYVAC vectors which can be used for this purpose, mention may be made of the vectors described in patents U.S. Pat. No. 5,942,235, U.S. Pat. No. 5,756,103 and U.S. Pat. No. 5,990,091; EP 83286, U.S. Pat. No. 5,494,807 and U.S. Pat. No. 5,762,938. In the context of the compositions which can be administered orally, use may also advantageously be made of bacterial vectors, such as lactobacillus or salmonella, expressing the polypeptide according to the invention and/or other HIV antigens, such as those conventionally used in the poxviruses described in the US patents above. The use of these bacterial vectors for immunization purposes is described in detail in International Journal of Food Microbiology 41 (1998) 155–167 by P. H. Pouwels et al. and Cell Vol. 91, 765–775, December 1997 by A. Darji et al., to which reference may be made for greater detail.

The present invention is also intended to cover a polypeptide, a conjugate or a vector as described above, and the pharmaceutical composition containing these compounds, for their use as a medicinal product, in particular for inducing specific neutralizing antibodies in a mammal. Since the antibodies induced have the property of neutralizing HIV primary isolates, the polypeptide according to the invention is therefore an antigen of interest for the prophylactic and therapeutic immunization of the human body against HIV-related infection.

The present invention therefore relates to a method for inducing specific neutralizing antibodies in a mammal, preferably humans, comprising administration of a pharmaceutical composition as defined above and induction of said specific humoral response.

The expression “a specific humoral response” is intended to mean a response comprising the production of antibodies directed specifically against the polypeptide according to the invention. The specific humoral response comprises the production of specific IgAs when the composition according to the invention is administered mucosally. The production of specific antibodies may be easily determined using conventional techniques well known to those skilled in the art, such as ELISA, RIA or Western blotting. The antibodies induced by the polypeptide according to the invention are capable of neutralizing many HIV primary isolates. This property may be determined using the neutralization test of C. Moog or of D. Montefiori.

The Applicant has demonstrated, surprisingly, that the polypeptide according to the invention is capable, after administration, of inducing antibodies capable of neutralizing HIV primary isolates. Said polypeptide therefore represents a valuable candidate for developing a vaccine which can be used for protecting and/or treating a large number of individuals at risk from or infected with HIV.

A subject of the invention is also a diagnostic method, comprising bringing a polypeptide according to the invention into contact with a biological sample and detecting the antibody/polypeptide complexes which are formed. HIV+ individuals in fact have anti-gp41 serum antibodies. An immunoassay (such as an ELISA assay in which the. polypeptide according to the invention is attached to the assay plate and then brought into contact with the serum to be tested, and the antibody/polypeptide complexes are then detected by colorimetry using a labeled second antibody) would therefore make it possible to diagnose infected individuals.

The present invention will be described in greater detail in the following examples, which are given purely by way of illustration of the invention and can in no way be considered to limit the scope of the latter.

EXAMPLE 1

Purification of the Polypeptide According to the Invention Cloning

The DNA sequence encoding the polypeptide SEQ ID No.4 was cloned in an inducible expression system.

The vector used is Pet-cer, which is constructed using the vector pET28 from Novagen. The commercial vector pET28c was amplified by PCR using 2 primers located on either side of the region corresponding to the F1 origin, such that the amplified product corresponds to virtually the entire vector of origin, minus the region comprising the F1 origin. The unique AscI and PacI restriction sites are provided, respectively, by the two primers which were used for the amplification. In parallel, the cer fragment is amplified using 2 primers which make it possible to obtain this fragment bordered by the AscI and PacI sites.

Vector and Cer fragment are digested with the AscI and PacI enzymes and then ligated to one another.

This vector in particular comprises an expression cassette under the control of the T7 promoter, a polylinker downstream of the T7 promoter for cloning the gene of interest, the CER fragment located downstream of the polylinker, making it possible to decrease multimerization of the plasmids, a T7 term transcription terminator and the kanamycin resistance gene. Positive regulation of the promoter is obtained in the presence of T7 RNA polymerase.

An approximately 0.5 Kb DNA fragment containing the sequence encoding the sequence SEQ ID No.3 is obtained by PCR using a plasmid containing the sequence encoding the HIV-1 LAI gp160.

The BspHI and XhoI restriction sites, used for the cloning, are respectively provided by the 5' 5' (5' gp41 SPF BspHI) and 3' (3'gp41TMBR/HSX) PCR primers. The 3' primer also contains the sequences encoding the polyhistidine chain and the flexible linkage which connects it to the polypeptide.

The PCR-amplified fragment was digested with the BspHI and XhoI enzymes and inserted into the expression vector digested with NcoI and XhoI (the NcoI and BspHI sites produce compatible protruding 5' ends after digestion).

The PCR amplification conditions are as follows: 97° C./30 s; 55° C./1 mm; 72° C./50 s; Taq DNA polymerase –25 cycles.

5' primer: 5'....*TC__ATG__*ACGCTGACGGTACAGGCC 3' (SEQ ID NO: 12)

3' primer: 5' CCG*CTCGAG*CTAATGGTGATGGTGATGGTGTGACCCTCCCCCTCCACTTGCCCATTTATCTAA 3' (SEQ ID NO: 13)

The BspHI and XhoI restriction sites are indicated in italics, the initiation codon ATG and termination codon TAG (complementary strand) are underlined and in bold characters.

The construct was characterized by restriction mapping and sequencing the 5' and 3' junctions and also all of the inserted fragment.

Tests for expression under conventional conditions made it possible to obtain and visualize, both after staining with Coomassie blue and Western blotting analysis using an anti-polyhistidine antibody, a product having an apparent molecular weight in accordance with the expected result.

Expression and Purification:

The plasmid thus obtained is expressed in *E. coli* BL21 lambda DE3. The *E. coli* cells are transformed with approximately 1 ng of plasmid. The culturing of *E. coli* BL21 DE 3 expressing the polypeptide is carried out in TB medium in the presence of kanamycin (25 μg/ml final concentration) with induction lasting 4 hours at 37° C., which begins by adding 1 mM of IPTG when the OD is approximately 0.9.

Expression of the polypeptide produces approximately 30 mg of purified polypeptide/1 of culture.

The bacteria are ruptured by sonication (4×2 min), avoiding heating the bacterial extracts. The polypeptide is then in the form of inclusion bodies. These inclusion bodies are recovered by centrifugation (for 30 min at 10 000 g, at 4° C.), and are then solubilized in a 50 mM Tris buffer at pH 8 containing 6M urea and 500 mM NaCl. The solution is filtered through a filter with a 0.45 μm porosity (Milex HV, Millipore) before chromatography on a nickel-sepharose column (Hi-trap, Pharmacia). The polypeptide is loaded onto the column in the presence of 10 mM imidazole in the Tris-Urea buffer. The column is washed under the same conditions, and the purified polypeptide is then eluted by injecting a 0.5 M solution of imidazole in the same buffer. The polypeptide is then dialyzed into a 50 mM formate buffer at pH 2.5 before chromatography on a reverse-phase column by HPLC, the role of which is to remove residual endotoxins.

After the polypeptide has been loaded, a gradient of 20 to 80% of acetonitrile containing 0.1% of TFA circulates through the semi-preparative column (214TP510, Vydac). The polypeptide is eluted between 40 and 60% of acetonitrile. The solvents are then removed by evaporation under a vacuum, and then by dialysis into a formate buffer at pH 2.5. The endotoxins are completely removed from the polypeptide obtained, the degree of purity of which is greater than 80%. It is stored at −45° C.

EXAMPLE 2

Determination of the Humoral Immunity After Parenteral Administration

The polypeptide SEQ ID No.4 was tested in guinea pigs, in rabbits and in Cynomolgus monkeys according to the protocols described below.

Guinea pigs: Groups of 5 guinea pigs were injected 3 times, at 3-week intervals, in the thighs (biceps femoris muscle) with 20 μg per dose of antigen. Upon each injection, the animals received 0.5 ml of the formulation (0.25 ml in each thigh).

Serum samples were taken from the animals in order to analyze the antibodies before immunization, and 3 and 2 weeks after the 2$^{nd}$ and 3$^{rd}$ immunizations, respectively.

The three compositions tested: antigen+alum (aluminum phosphate, 6 mg per dose); antigen+alginate; and antigen in arginine buffer+alginate were prepared in the following way:

a- For the formulations adjuvanted with aluminum phosphate: the antigen is in 50 mM formate medium, pH 2.5. The formulations are obtained by adding the alum to the antigen composition and incubating with gentle agitation for 30 minutes. The mixture is then centrifuged (5 minutes at 3 000 rpm), the supernatant being removed and replaced with PBS buffer so as to obtain a final concentration of 500 μl/dose. Resuspension is carried out using an ultrasound bath.

b- For the formulation in alginate: the antigen is in 50 mM formate medium, pH 2.5. A filtered 1% solution of alginate (LVM grade, PRONOVA) in PBS buffer is added to this so as to be at 1.4:1 (vol. antigen/vol. alginate). After incubation at ambient temperature (5 minutes), the volume of the mixture is made up with a solution of Tween 80, 0.67% by weight in PBS buffer, so as to obtain a final concentration of 50 μl/dose. Homogenization is carried out by slight vortexing.

c- For the formulation in arginine+alginate: the antigen is in a medium of 1 M arginine and PBS, pH 7.4. The preparation is the same as described in b-, with use, in this case, of a 2.75:1 (vol. antigen: vol. alginate) ratio.

Rabbits: Groups of 2 rabbits were injected 3 times, at 3-week intervals, in the thighs with 40 μg per dose of antigen. Upon each injection, the animals received 1 ml of the formulation.

Serum samples were taken from the animals in order to analyze the antibodies before immunization, and then 3 and 2 weeks after the 2$^{nd}$ and 3$^{rd}$ immunizations, respectively.

d- The composition tested here: antigen+alum (aluminum phosphate, 6 mg per dose) was prepared in the following way: aluminum phosphate is added to the antigen in 50 mM formate medium, pH 2.5, the entire mixture being incubated for 30 minutes at +4° C. with gentle agitation (turning wheel). The tubes containing these preparations are then centrifuged (5 minutes at 3 000 rpm), the supernatant being removed and replaced with PBS buffer so as to obtain a final concentration of 1 ml/dose. Resuspension is carried out using an ultrasound bath.

Rhesus monkeys (*macaca fascicularis*): Groups of 2 monkeys were injected 3 times, at 1-month intervals, in the thighs (rectus femoris muscle) with 100 μg per dose of antigen adsorbed onto 6 ml of alum (aluminum phosphate). Upon each injection, the animals received 1 ml of the formulation.

Serum samples were taken from the animals in order to analyze the antibodies before immunization, and then 4 and 2 weeks after the 2$^{nd}$ and 3$^{rd}$ immunizations, respectively.

The composition tested here: antigen+alum was prepared in the following way: aluminum phosphate is added to the antigen in 50 mM formate medium, pH 2.5, the entire mixture being incubated for 30 minutes at 4° C. with gentle agitation (turning wheel). The tubes containing these preparations are then centrifuged (5 minutes at 3 000 rpm), the supernatant being removed and replaced with PBS buffer so as to obtain a final concentration of 1 ml/dose. Resuspension is carried out using an ultrasound bath.

The results are given in the tables below:

As shown in table 1, the polypeptide induces significant, homogeneous and specific ELISA antibody levels against the polypeptide according to the invention and gp160

MN/LAI-2 (hybrid glycoprotein in which the gp120 subunit derives from the HIV-1 MN isolate and the gp41 subunit derives from the HIV-1 LAI isolate). These IgG responses virtually reach a plateau as soon as the $2^{nd}$ injection (table 1). The formulation in alginate appears to be 10 times less effective, in terms of specific antibody levels induced, than the formulation in alum.

TABLE 1

Guinea pig test - Antibody responses by ELISA

| Immunogen | Anti-SEQ ID No. 4 IgG: Post-2* IgG titers ($log_{10}$) (number of positives) | Anti-SEQ ID No. 4 IgG: Post-3* IgG titers ($log_{10}$) (number of positives)) | Anti-gp160 MN/LAI-2 IgG: Post-2* IgG titers ($log_{10}$) (number of positives) | Anti-gp160 MN/LAI-2 IgG: Post-3* IgG titers ($log_{10}$) (number of positives) |
|---|---|---|---|---|
| polypeptide (alum) | 5.4 ± 0.1 (5+/5) | 5.5 ± 0.2 (5+/5) | 5.1 ± 0.2 (5+/5) | 5.6 ± 0.2 (5+/5) |
| polypeptide (alginate) | 4.5 ± 0.2 (5+/5) | 4.6 ± 0.1 (5+/5) | 4.1 ± 0.3 (5+/5) | 4.4 ± 0.3 (5+/5) |
| polypeptide (PBS arginine/alginate) | 4.3 ± 0.2 (5+/5) | 4.7 ± 0.2 (5+/5) | 3.8 ± 0.3 (5+/5) | 4.3 ± 0.2 (5+/5) |

*Geometric mean ± standard deviation ($log_{10}$)

NB: All the preimmune sera tested are below the detection threshold (i.e. 1.9 $log_{10}$ for the anti-gp160 ELISA and 1.0 $log_{10}$ for the anti-polypeptide ELISA).

The neutralizing activity of the post-$3^{rd}$ immunization sera was then evaluated initially with respect to the HIV-1 MN laboratory strain, on individual sera (at the DC Montefiori laboratory). As shown by the results obtained, no neutralization of the MN strain was observed.

The neutralizing activity of the post-3 sera was also evaluated with respect to primary HIV-1 strains (laboratories of C. Moog and of D. Montefiori) (table 2). The analysis was carried out on individual sera. Advantageously, contrary to that which was observed for the MN strain, the guinea pigs showed significant neutralizing activities against several of the viral strains tested.

TABLE 2

Guinea pig test - Anti-HIV-1 neutralizing antibody responses

| Immunogen | Laboratory strain: MN§ | Primary isolates: Bal§ | SF162§ | 5768§ | Pavo§ | Bx08¤ | Bx17¤ |
|---|---|---|---|---|---|---|---|
| polypeptide (alum) | <20 | between 90% and 98% | 97% | between 94% and 99% | between 96% and 99% | between 8 and 16 | between 8 and 10 |
| polypeptide (PBS arginine/alginate) | NT | NT | NT | NT | NT | 4 | NT |

§Lab. D. Montefiori: Results given for the post-3 sera (arithmetic value or %)

¤Lab. C. Moog: Results given for the post-3 sera (arithmetic value)

NT: Not tested

NB: All the preimmune sera tested are below the positivity threshold (i.e., depending on the methods: <20 for the HIV-1 MN strain and <80% or <4 for the primary isolates).

TABLE 3

| | Rabbit test - ELISA antibody responses | |
|---|---|---|
| | Anti-SEQ ID No. 4 IgG | |
| Immunogen | Post-2* IgG titers ($log_{10}$) (number of positives) | Post-3* IgG titers ($log_{10}$) (number of positives) |
| Polypeptide (in alum) | 4.9 ± 0.04 (2+/2) | 5.1 ± 0.1 (2+/2) |

TABLE 4

| | Monkey test - ELISA antibody responses | |
|---|---|---|
| | Anti-SEQ ID No. 4 IgG | |
| Immunogen | Post-2* IgG titers ($log_{10}$) (number of positives) | Post-3* IgG titers ($log_{10}$) (number of positives) |
| Polypeptide (in alum) | 5.3 ± 0.4 (2+/2) | 5.6 ± 0.1 (2+/2) |

NB: The preimmune sera tested prove to be below the positivity threshold (1.0 $log_{10}$).

The results given above clearly show that the polypeptide according to the invention is capable of inducing significant specific ELISA antibody levels in all the animal species tested. These IgG responses increased slightly between the $2^{nd}$ and $3^{rd}$ injection.

These antibodies, which have the property of neutralizing primary isolates, make the polypeptide according to the invention a valuable candidate for immunization in humans.

EXAMPLE 3

Determination of the Humoral Immunogenicity of the Polypeptide According to the Invention Administered Mucosally The polypeptide SEQ ID No.4 was tested in BALB/c mice according to the protocol described below.

BALB/c mice: Groups of 6 to 7 mice were administered intrabuccally or intragastrically 3 times, at 2-week intervals, and once 1 month later, with 50 µg per dose of antigen alone or formulated with 5 µg of cholera toxin (CT). gp160 MN/LAI-2 was added as a control, formulated with 5 µg of cholera toxin (CT). On each administration, the animals received either 20 µl, for the intrabuccal administration, or 50 µl, for the intragastric administration, of the formulation.

The compositions tested were prepared in the following way: for the gp160 antigen: the required volume of a solution of CT at 2 mg/ml in $H_2O$, to which PBS buffer is added so as to have the final concentration of 20 or 500 µl/dose, is added. The antigen SEQ ID No.4, in 50 mM formate medium, pH 2.5, is first diluted in 50 mM formate and then a solution of CT at 2 mg/ml in $H_2O$ is added to it so as to have the final concentration of 20 or 500 µl/dose.

Serum samples and vaginal secretion samples were taken from the animals in order to analyze the antibodies before immunization, and then 2 weeks after the $4^{th}$ immunization.

The IgG and IgA responses induced in the vaginal secretions, specific for the polypeptide, were evaluated by ELISA and normalized, respectively, with the total IgGs and IgAs contained in these mucosal samples. The IgG antibody responses specific for the polypeptide, induced in the sera, were also evaluated by ELISA.

As shown in table 5 below, the polypeptide according to the invention induced specific serum IgG responses after gastric or buccal administration. For these 2 routes, the antibody titers are approximately 10 times greater when the polypeptide is administered in the presence of CT, compared to antigen alone. However, it is interesting to note that, even in the absence of CT, a significant humoral response is induced by the polypeptide. The buccal route proved, overall, to be more immunogenic than the gastric route. Contrary to the polypeptide, gp160 MNLAI-2, in the presence of CT, induced no or virtually no antibodies against the various antigens tested (polypeptide, gp120 MN [produced by Agmed] and V3 MN), this being whatever the route of immunization.

TABLE 5

| | | Mouse test - ELISA antibody responses in the sera | | |
|---|---|---|---|---|
| Immunization route | Immunogen | Anti-Seq ID No. 4 IgG Post-4* IgG titers ($log_{10}$) (number of positives) | Anti-gp120 MN IgG Post-4* IgG titers ($log_{10}$) (number of positives) | Anti-V3 MN IgG Post-4* IgG titers ($log_{10}$) (number of positives) |
| Gastric | gp160 MN/LAI-2 (+ CT) | 1.5 ± 1.1 (1+/5) | 2.7 ± 1.4 (2+/5) | 1.3 ± 0.7 (1+/5) |
| | polypeptide | 2.2 ± 1.2 (5+/6) | NT | NT |
| | polypeptide (+ CT) | 3.5 ± 0.9 (7+/7) | NT | NT |
| Buccal | gp160 MN/LAI-2 (+ CT) | 1.0 ± 0.0 (0+/4) | 1.9 ± 1.9 (0+/4) | 1.0 ± 1.0 (0+/4) |
| | polypeptide | 2.9 ± 1.1 (6+/7) | NT | NT |
| | polypeptide (+ CT) | 4.0 ± 0.7 (7+/7) | NT | NT |

*Geometric mean ± standard deviation ($log_{10}$);
NT: Not tested
NB: All the preimmune sera tested are below the detection threshold (i.e. 1.9 $log_{10}$ for the anti-gp120 ELISA and 1.0 $log_{10}$ for the anti-polypeptide and anti-V3 ELISAs).

As shown in table 6 below, the polypeptide according to the invention provoked specific IgA and/or IgG responses in the mucosal secretions tested.

In terms of the vaginal secretions, the polypeptide administered either buccally or gastrically was capable, with or with CT, of provoking IgA and IgG responses, the responses being, however, more frequent in the presence of CT. It may be noted that the gp160 MN/LAI-2+CT provoked no or very few mucosal responses, as observed in the serum.

TABLE 6

Mouse test - ELISA antibody responses in the mucosal secretions

| | | Vaginal secretions | |
|---|---|---|---|
| Immunization route | Immunogen | Anti-polypeptide IgA/total IgA ratio* (number of positives) | Anti-polypeptide IgG/total IgG ratio* (number of positives) |
| Gastric | gp160 MN/LAI-2 (+CT) | 0.6 ± 1.2 (1+/5) | 0.2 ± 0.4 (1+/5) |
| | polypeptide | 3.7 ± 7.4 (6+/7) | 2.8 ± 5.2 (2+/7) |
| | polypeptide (+CT) | 5.8 ± 5.8 (6+/7) | 8.3 ± 9.3 (6+/7) |
| Buccal | gp160 MN/LAI-2 (+CT) | 0.0 ± 0.0 (0+/4) | 0.0 ± 0.0 (0+/4) |
| | polypeptide | 1.3 ± 1.5 (4+/7) | 1.2 ± 2.9 (2+/7) |
| | polypeptide (+CT) | 14.5 ± 14.5 (7+/7) | 7.2 ± 10.2 (4+/7) |

*Mean of the ratios of the mice of each group × $10^3$, the ratio being defined as the anti-polypeptide IgG or IgA titer (in arbitrary units) divided by the total IgG or IgA titer (in ng/ml), respectively.

The examples above show that the polypeptide according to the invention is capable of inducing, in all the animal species tested, after parenteral administration, significant specific serum IgG responses against the polypeptide and the gp160 MN/LAI-2. The antibodies induced have activity capable of neutralizing several HIV primary isolates.

The examples above also show that the polypeptide according to the invention is capable of inducing, after mucosal administration, serum IgG antibodies and mucosal IgG and IgA antibodies in vaginal secretions.

EXAMPLE 4

Determination of the Humoral Immunogenicity of Plasmid DNA Vectors Encoding a Polypeptide According to the Invention Administered Intramuscularly Four different plasmids were prepared and tested in order to determine their immunogenicity. These plasmids are:

with TPA for: human tPA signal sequence, SPF for: without fusion peptide, PK for: the Kennedy neutralizing epitope, i.e. ERDRD, located in the intracytoplasmic portion of gp41 at position 746–750, within the "Kennedy peptide" sequence located between residues 731–752 (Kennedy et al., 1986, Science, 231: 1556–59; (Vella et al., 1993, J. General Virology, 74: 2603–07).

The sequences encoding the polypeptides tested were amplified by PCR and cloned into a derivative of the expression vector pCAMycHis (Invitrogen). The modified vector used is obtained by replacing the existing polylinker with a different "polylinker" containing the XbaI and BamHI restriction sites, into which is inserted the sequence encoding the antigen tested. The expression of the cloned gene is under the control of the CMV promoter. The DNA is prepared after transformation of an *E. coli* strain XL-1 blue. A 2-liter culture (LB medium+carbenicillin at 100 mg/ml) makes it possible to obtain approximately 10 mg of plasmid. After alkaline lysis, the plasmid is purified on a Qiagen column (Gigaprep) according to the protocol indicated by the supplier.

The immunogenicity of the constructs thus obtained is evaluated -in guinea pigs according to the following protocol: groups of 5 guinea pigs were injected 4 times, at 1-month intervals, in the thighs (biceps femoris muscle) with 200 μg per dose of plasmid. Upon each injection, the animals received 1 ml of the formulation (0.5 ml in each thigh).

Serum samples were taken from the animals in order to analyze the antibodies before immunization, and then 1 month after the $4^{th}$ immunization.

The results are given in the tables below:

As shown in table 7, the plasmid PCA TPA gp41 SPF PK proved to be the most immunogenic, capable of inducing significant levels of antibodies specific for the polypeptide according to the invention, also recognizing gp160 MN LAI-2. The humoral responses induced by the other constructs tested proved to be weaker. These results indicate that the absence of fusion peptide and the addition of the neutralizing epitope of the Kennedy peptide both appear to play an important role in the humoral immunogenicity of the plasmid.

TABLE 7

Guinea pig test - Antibody responses by ELISA

| Immunogen | Anti-SEQ ID No. 4 IgG Post-4* IgG titers ($log_{10}$) (number of positives) | Anti-gp160 MN/LAI-2 IgG Post-4* IgG titers ($log_{10}$) (number of positives) |
|---|---|---|
| PCA TPA gp41 PK | 1.2 ± 0.4 (1+/5) | 1.9 ± 0.0 (0+/5) |

PCA TPA gp41 PK (antigen tested from the N- to the C-terminal: AA1-AA157-GGRERDRDRSGGGGS; SEQ ID NO: 11)

PCA TPA gp41 SPF PK (antigen tested from the N- to the C- terminal: AA25-AA157-GGRERDRDRSGGGGS; SEQ ID NO: 11)

PCA TPA gp41 (antigen tested from the N- to the C- terminal: AA1-AA157)

PCA TPA gp41 SPF (antigen tested from the N- to the C- terminal: AA25-AA157)

TABLE 7-continued

Guinea pig test - Antibody responses by ELISA

| Immunogen | Anti-SEQ ID No. 4 IgG Post-4* IgG titers ($log_{10}$) (number of positives) | Anti-gp160 MN/LAI-2 IgG Post-4* IgG titers ($log_{10}$) (number of positives) |
|---|---|---|
| PCA TPA gp41 SPF PK | 3.2 ± 0.6 (4+/4) | 3.4 ± 0.7 (4+/4) |
| PCA TPA gp41 | 1.0 ± 0.0 (0+/5) | 1.9 ± 0.0 (0+/5) |
| PCA TPA gp41 SPF | 1.2 ± 0.5 (1+/5) | NT |

*Geometric mean ± standard deviation ($log_{10}$)
NB: All the preimmune sera tested are below the detection threshold (i.e. 1.9 $log_{10}$ for the anti-gp160 ELISA and 1.0 $log_{10}$ for the anti-polypeptide ELISA).

The results of primary isolate neutralization indicated in table 8 below show that the plasmid PCA TPA gp41 SPF PK is the most effective in terms of neutralization, the best results being obtained with the constructs lacking the gp41 fusion peptide.

TABLE 8

Guinea pig test - Anti-HIV-1 neutralizing antibody responses

| Immunogen | Bx08 | Bx17 |
|---|---|---|
| PCA TPA gp41 PK | 4 | <4 |
| PCA TPA gp41 SPF PK | >4 and < or = 16 | 8 |
| PCA TPA gp41 | 5 | <4 |
| PCA TPA gp41 SPF | >4 and <16 | 8 |

¤Lab. C. Moog: Results given for the post-3 sera (arithmetic value)
NT: Not tested.

The invention claimed is:

1. A method for inducing antibodies neutralizing HIV primary isolates in a mammal, comprising administration of a pharmaceutical composition comprising a polypeptide represented by the formula:

N-L-C in which:

N represents the amino acid sequence 25–81 of gp41,

C represents the amino acid sequence 112–157 of gp41, and

L represents a flexible linking sequence consisting of from 2 to 30 amino acids.

2. The method as claimed in claim 1, in which N represents SEQ ID No.1 and C represents SEQ ID No.2.

3. The method as claimed in claim 1, wherein the polypeptide has the sequence SEQ ID No.3.

4. The method as claimed in any one of the preceding claims, wherein the polypeptide further comprises a sequence containing the epitope ERDRD (SEQ ID NO: 9) at its N or COOH-terminal end.

5. The method as claimed in claim 4 wherein the polypeptide has the sequence SEQ ID No.4.

6. The method as claimed in claim 2, wherein the polypeptide has the sequence SEQ ID No.3.

7. The method as claimed in claim 6, wherein the polypeptide further comprises a sequence containing the epitope ERDRD (SEQ ID NO: 9) at its N or COOH-terminal end.

8. The method as claimed in claim 7 wherein the polypeptide has the sequence SEQ ID No.4.

* * * * *

UNITED STATES PATENT AND TRADEMARK OFFICE

CERTIFICATE OF CORRECTION

PATENT NO. : 7,056,519 B2
APPLICATION NO. : 10/438691
DATED : September 6, 2006
INVENTOR(S) : Florence Boudet et al.

It is certified that error appears in the above-identified patent and that said Letters Patent is hereby corrected as shown below:

Title Page, Item 56
OTHER PUBLICATIONS, 4th citation, delete "Immunofeficiency" and insert therefore --Immunodeficiency--

Title Page, Item 56
OTHER PUBLICATIONS, 6th citation, delete "Immunodificiency" and insert therefore --Immunodeficiency--

Title Page, Item 56
OTHER PUBLICATIONS, 14th citation, delete "Petptides" and insert therefore --Peptides--

Column 4, line 28, delete "et P E Dawson" and insert therefore --and P E Dawson--

Column 5, line 25, delete "inducicble" and insert therefore --inducible--

Column 10, line 37, 5' is repeated, delete the extra "5'"

Column 10, line 47, delete "C./1 mm" and insert therefore --C./1 m--

Column 12, line 39, delete "Rhesus monkeys" and insert therefore --Cynomolgus monkeys--

Column 13, Table 1, "(number of positives))" has two parenthesis delete the extra ")"

Column 17, line 5-6, delete "with or with" and insert therefore --with or without--

UNITED STATES PATENT AND TRADEMARK OFFICE

CERTIFICATE OF CORRECTION

PATENT NO. : 7,056,519 B2 
APPLICATION NO. : 10/438691
DATED : September 6, 2006
INVENTOR(S) : Florence Boudet et al.

It is certified that error appears in the above-identified patent and that said Letters Patent is hereby corrected as shown below:

Column 18, line 22, delete “evaluated -in” and insert therefore --evaluated in--

Signed and Sealed this

Twenty-first Day of November, 2006

JON W. DUDAS
*Director of the United States Patent and Trademark Office*

UNITED STATES PATENT AND TRADEMARK OFFICE

CERTIFICATE OF CORRECTION

PATENT NO. : 7,056,519 B2

APPLICATION NO. : 10/438691
DATED : June 6, 2006
INVENTOR(S) : Florence Boudet et al.

It is certified that error appears in the above-identified patent and that said Letters Patent is hereby corrected as shown below:

Title Page, Item 56
OTHER PUBLICATIONS, 4th citation, delete “Immunofeficiency” and insert therefore --Immunodeficiency--

Title Page, Item 56
OTHER PUBLICATIONS, 6th citation, delete “Immunodificiency” and insert therefore --Immunodeficiency--

Title Page, Item 56
OTHER PUBLICATIONS, 14th citation, delete “Petptides” and insert therefore --Peptides--

Column 4, line 28, delete “et P E Dawson” and insert therefore --and P E Dawson--

Column 5, line 25, delete “inducicble” and insert therefore --inducible--

Column 10, line 37, 5’ is repeated, delete the extra “5’”

Column 10, line 47, delete “C./1 mm” and insert therefore --C./1 m--

Column 12, line 39, delete “Rhesus monkeys” and insert therefore --Cynomolgus monkeys--

Column 13, Table 1, “(number of positives))” has two parenthesis delete the extra “)”

Column 17, line 5-6, delete “with or with” and insert therefore --with or without--

UNITED STATES PATENT AND TRADEMARK OFFICE

CERTIFICATE OF CORRECTION

PATENT NO. : 7,056,519 B2
APPLICATION NO. : 10/438691
DATED : June 6, 2006
INVENTOR(S) : Florence Boudet et al.

It is certified that error appears in the above-identified patent and that said Letters Patent is hereby corrected as shown below:

Column 18, line 22, delete “evaluated -in” and insert therefore --evaluated in--

This certificate supersedes Certificate of Correction issued November 21, 2006.

Signed and Sealed this

Second Day of January, 2007

JON W. DUDAS
*Director of the United States Patent and Trademark Office*